(12) United States Patent
Lear et al.

(10) Patent No.: US 10,702,262 B1
(45) Date of Patent: Jul. 7, 2020

(54) HEMI-BRIDGE AND METHODS OF MANUFACTURING AND USING SAME

(71) Applicant: SUTUREGARD Medical, Inc., Portland, OR (US)

(72) Inventors: William Lear, Corvallis, OR (US); Daniel A Ladizinsky, Lake Osewgo, OR (US); Jennifer Akeroyd, Corvallis, OR (US)

(73) Assignee: SUTUREGARD Medical, Inc., Portland, OR (US)

( * ) Notice: Subject to any disclaimer, the term of this patent is extended or adjusted under 35 U.S.C. 154(b) by 0 days.

(21) Appl. No.: 16/576,907

(22) Filed: Sep. 20, 2019

Related U.S. Application Data

(60) Provisional application No. 62/836,341, filed on Apr. 19, 2019, provisional application No. 62/876,849, filed on Jul. 22, 2019.

(51) Int. Cl.
| | | |
|---|---|---|
| *A61B 17/04* | (2006.01) | |
| *A61B 17/06* | (2006.01) | |
| *A61F 13/02* | (2006.01) | |

(52) U.S. Cl.
CPC ...... *A61B 17/0466* (2013.01); *A61B 17/0401* (2013.01); *A61B 17/0487* (2013.01); *A61B 17/06166* (2013.01); *A61F 13/023* (2013.01); *A61F 13/0246* (2013.01); *A61B 2017/0495* (2013.01); *A61B 2017/0496* (2013.01); *A61B 2017/06033* (2013.01)

(58) Field of Classification Search
CPC ............ A61B 17/0466; A61B 17/0487; A61B 17/06166; A61F 13/023; A61F 13/0246
See application file for complete search history.

(56) References Cited

U.S. PATENT DOCUMENTS

| | | | |
|---|---|---|---|
| 1,969,188 A | 8/1934 | Spicer | |
| 2,387,131 A | 10/1945 | Gomez | |
| 3,698,395 A | 10/1972 | Hasson | |
| 3,976,079 A | 8/1976 | Samuels et al. | |
| 4,539,990 A | 9/1985 | Stivala | |
| 5,207,703 A * | 5/1993 | Jain .................. | A61B 17/06061 606/232 |
| 5,665,108 A | 9/1997 | Galindo | |
| 5,843,123 A | 12/1998 | Brazeau | |
| 6,726,706 B2 | 4/2004 | Dominguez | |
| 6,736,823 B2 * | 5/2004 | Darois ................. | A61F 2/0063 600/37 |
| 7,361,185 B2 | 4/2008 | O'Malley et al. | |
| 7,429,265 B2 | 9/2008 | O'Malley et al. | |
| 9,554,799 B2 | 1/2017 | Belson et al. | |

(Continued)

FOREIGN PATENT DOCUMENTS

| | | |
|---|---|---|
| KR | 1020140020993 A | 2/2014 |
| KR | 101758236 B1 | 7/2017 |
| KR | 101768878 B1 | 8/2017 |

*Primary Examiner* — Richard G Louis
(74) *Attorney, Agent, or Firm* — Wei & Sleman LLP

(57) ABSTRACT

A suture elevating device includes an insert having at least one eyelet, an upper layer of material at least partially disposed over the insert, and a lower layer of material disposed below the insert, the lower layer of material having an adhesive disposed on a lower surface, wherein the insert, the upper layer and the lower layer form three zones, each of the three zones having a different elasticity and stiffness than others of the three zones.

15 Claims, 13 Drawing Sheets

(56) References Cited

U.S. PATENT DOCUMENTS

| | | | |
|---|---|---|---|
| 2002/0198565 A1* | 12/2002 | Dominguez | A61B 17/0466 |
| | | | 606/228 |
| 2003/0078617 A1* | 4/2003 | Schwartz | A61F 2/30749 |
| | | | 606/230 |
| 2003/0212462 A1* | 11/2003 | Gryska | A61F 2/0063 |
| | | | 623/23.72 |
| 2006/0116696 A1* | 6/2006 | Odermatt | A61L 31/10 |
| | | | 606/151 |
| 2015/0018874 A1 | 1/2015 | Riskin et al. | |
| 2016/0249924 A1 | 9/2016 | Belson et al. | |
| 2016/0310140 A1 | 10/2016 | Belson et al. | |
| 2017/0014124 A1 | 1/2017 | Lear | |

\* cited by examiner

HEMI-BRIDGE AND METHODS OF MANUFACTURING AND USING SAME

CROSS-REFERENCE TO RELATED APPLICATIONS

This application claims priority to U.S. Provisional Application Ser. No. 62/836,341, filed Apr. 19, 2019, and U.S. Provisional Application Ser. No. 62/876,849, filed Jul. 22, 2019, the contents of which are hereby incorporated by reference in their entirety as if fully set forth herein.

FIELD OF THE DISCLOSURE

The present disclosure relates generally to wound closure and methods and devices for improving same. More specifically, the present disclosure relates to a hemi-bridge device and methods for facilitating wound closure using same.

BACKGROUND OF THE DISCLOSURE

Sutures are stitches used to close open wounds and/or surgical incisions of a patient. A medical practitioner generally uses a needle with an attached thread to substantially sew two adjacent sections of skin together to close the wound or incision. Surgical knots are often used to secure the sutures and ensure proper healing. Sutures and surgical knots contacting the skin can be inflammatory and/or become "ingrown" and actually impede healing of the wound or incision. Additionally, complications may arise if the suture is tied too tightly or too loosely. Moreover, traditional techniques may leave unsightly "track marks."

Closure may be difficult, especially in high-tension areas of the skin, such where skin overlies the shoulder, knee, angle of the mandible, etc. Wound eversion occurs when the two wound surfaces are horizontally opposed into one another such that the closed incision is under no tension and topographically lies in a plane above the resting horizontal skin plane. Wound closures with maximal eversion resist excessive widening of the scar due to ongoing ambient stresses in the high-tension area during the wound healing and scar maturation processes. However, wound eversion can be technically difficult to achieve for less skilled operator, and a device to facilitate this is desirable. Further, there may be excessive tension on closures where an excisional defect is present in the skin. When suture is placed under excessive tension to close such wounds, the suture itself can slice through the skin ("cheesewiring").

Moreover, adhesive dressings of uniform elasticity impart shear force to the skin, greatest at the point of the dressing farthest from the source of the tension, which increases the risk of blistering. There is a need for an adhesive dressing of variable elasticity such that the elasticity at the end of the dressing farthest from the source of tension moves with a skin-like elasticity and thus reduces the risk of blistering.

Thus, there exists a need for suture devices that improve upon and advance the known suturing and dressing techniques.

SUMMARY OF THE DISCLOSURE

In at least some examples, a suture elevating device includes an insert having at least one eyelet, an upper layer of material at least partially disposed over the insert, and a lower layer of material disposed below the insert, the lower layer of material having an adhesive disposed on a lower surface, wherein the insert, the upper layer and the lower layer form three zones, each of the three zones having a different elasticity and stiffness than others of the three zones.

a suture elevating device includes an insert having a first end and a second end, the second being more elevated than the first end, the insert having a stair-shaped configuration including a lower step, an upper step and a ramp connecting the lower step to the upper step, the upper step and the lower step each having an eyelet, an upper layer of material disposed on the insert, a lower layer of material disposed below the insert, the lower layer of material having an adhesive disposed on a lower surface, and a plurality of longitudinally-oriented filaments at least partially located through at least one of the upper layer and the lower layer.

In some examples, a suture elevating device includes an insert having a first end and a second end, the second being more elevated than the first end, the insert having a stair-shaped configuration including a lower step, an upper step and a ramp connecting the lower step to the upper step, the upper step and the lower step each having an eyelet, an upper layer of material at least partially disposed over the insert, and a lower layer of material disposed below the insert, the lower layer of material having an adhesive disposed on a lower surface.

BRIEF DESCRIPTION OF THE DISCLOSURE

Various embodiments of the presently disclosed hemi-bridges are disclosed herein with reference to the drawings, wherein.

Figure 5A:
Figure 5B:
Figure 5C:
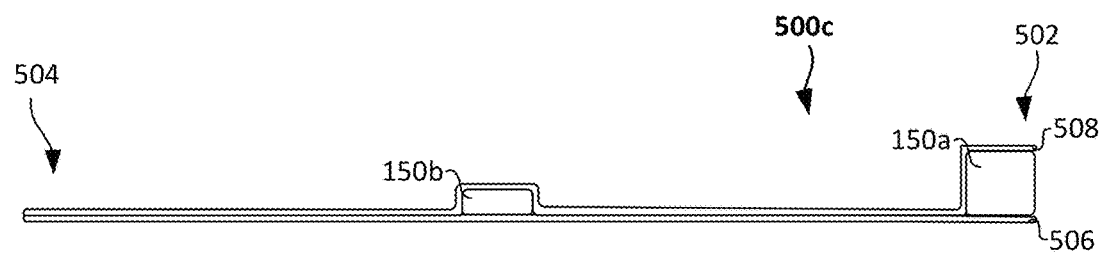
Figure 6:
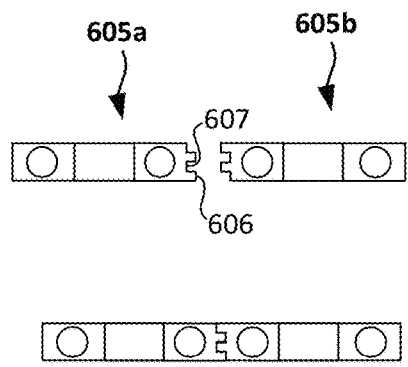
Figure 7:
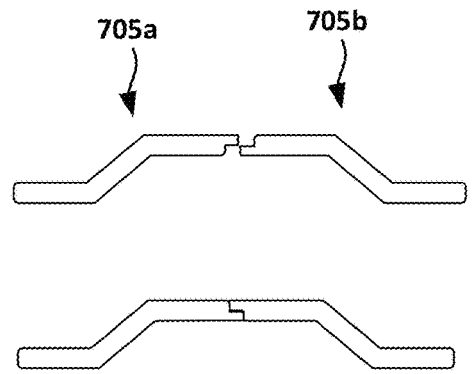
Figure 8:
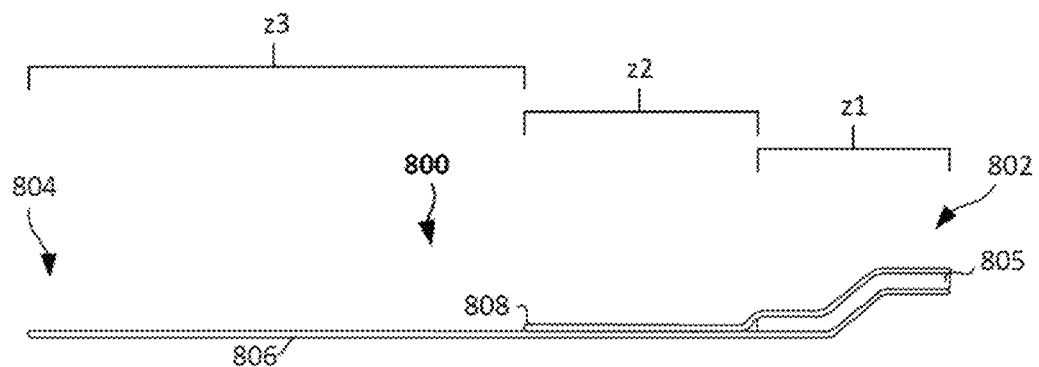
Figure 9:
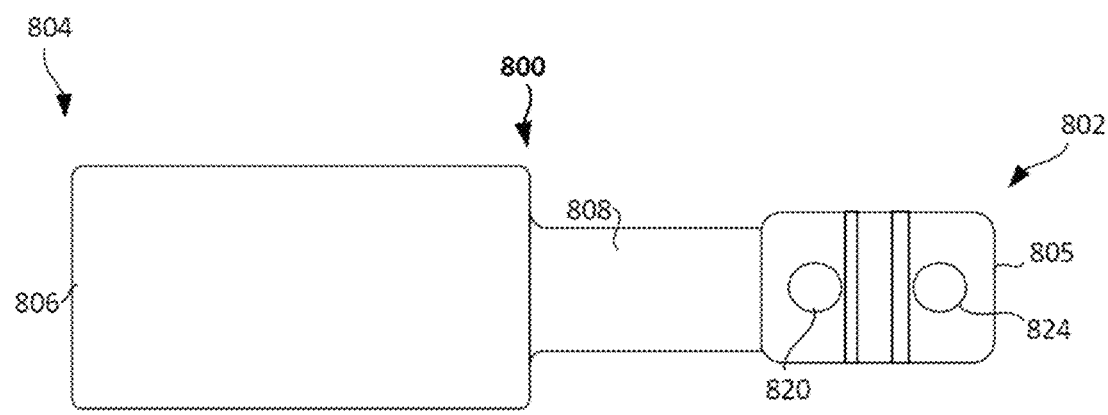
Figure 10:
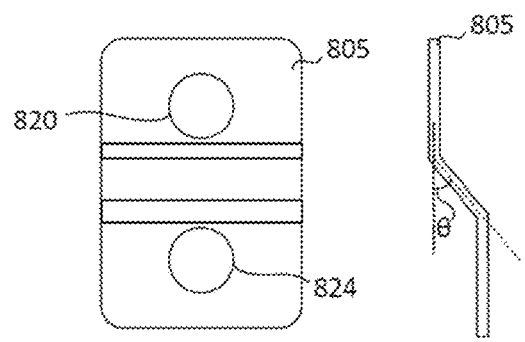
Figure 11:
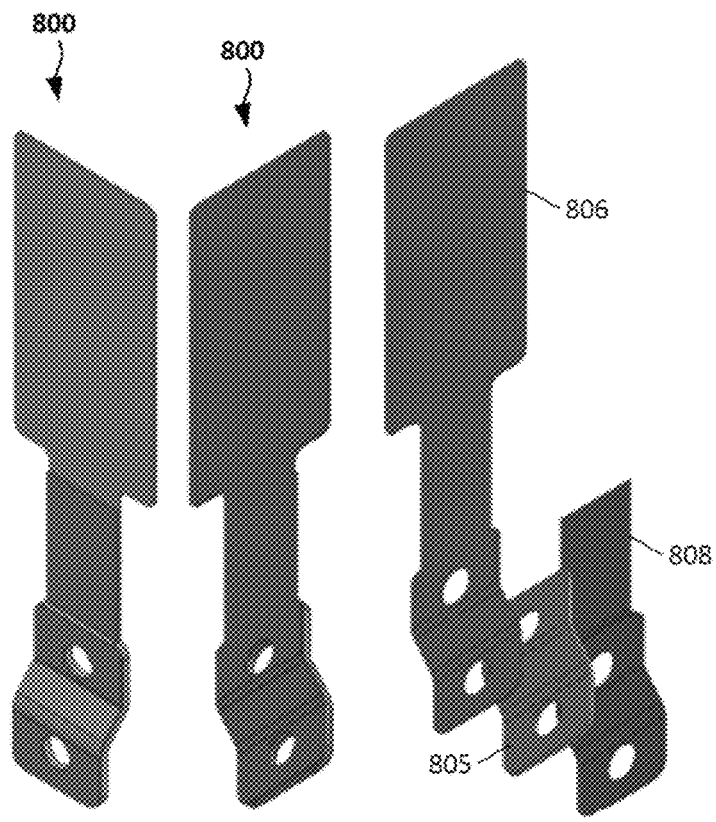
Figure 12:
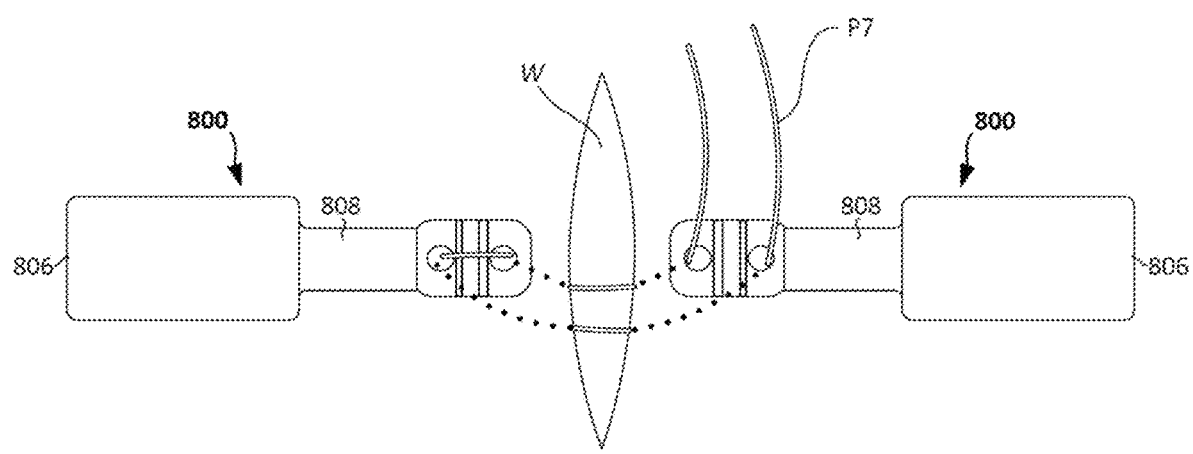
Figure 13A:
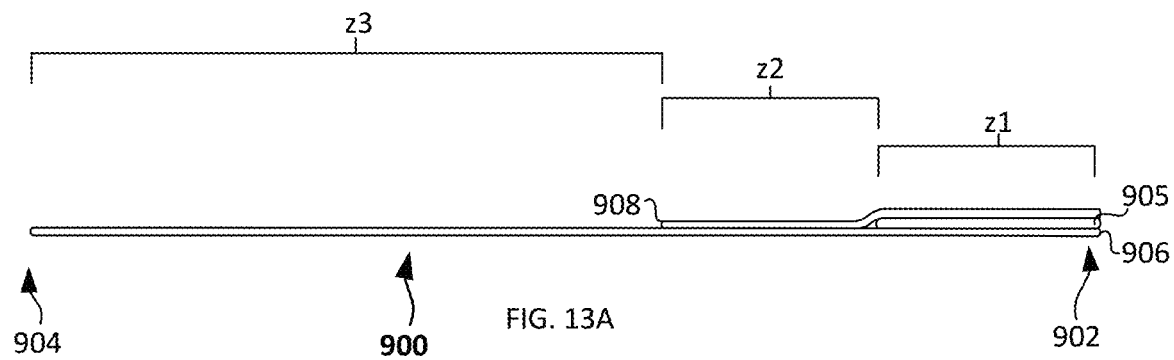
Figure 13B:
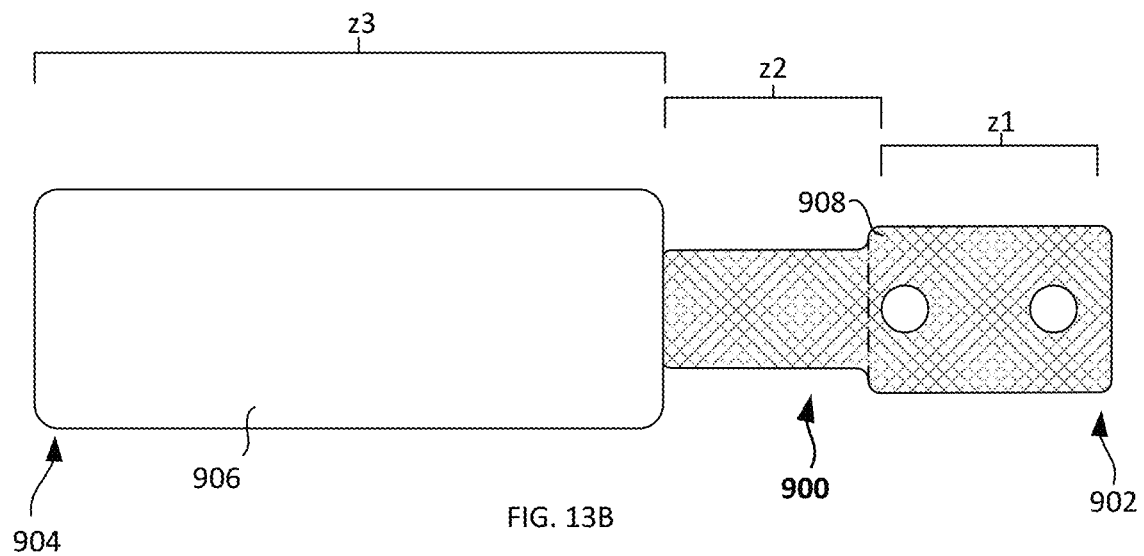
Figure 13C:
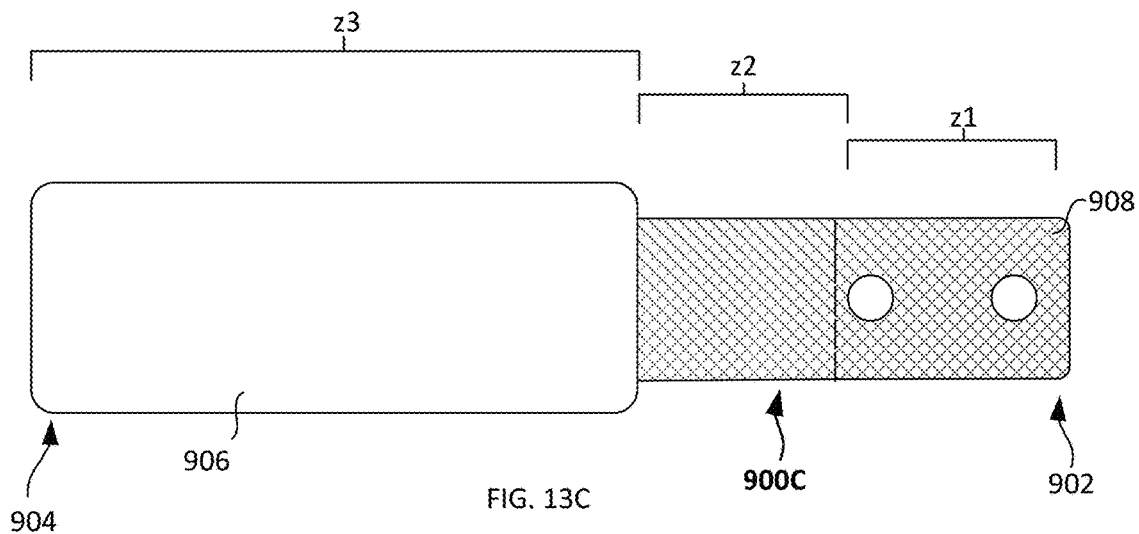
Figure 13D:
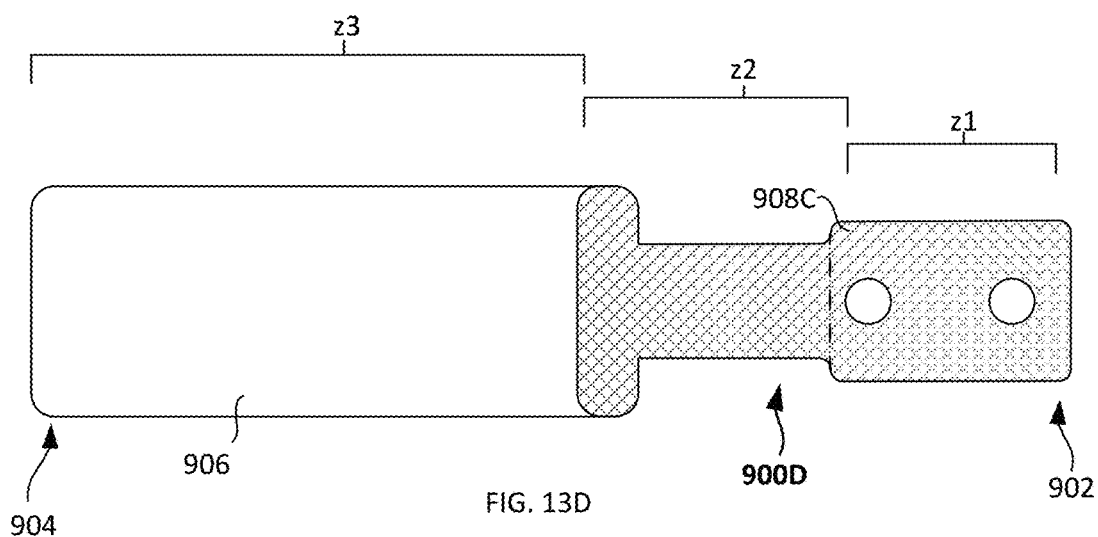
Figure 13E:
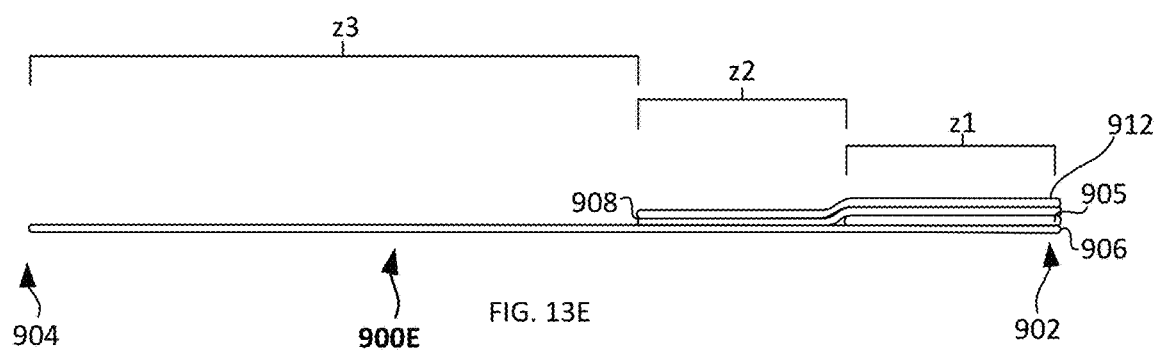
Figure 14A:
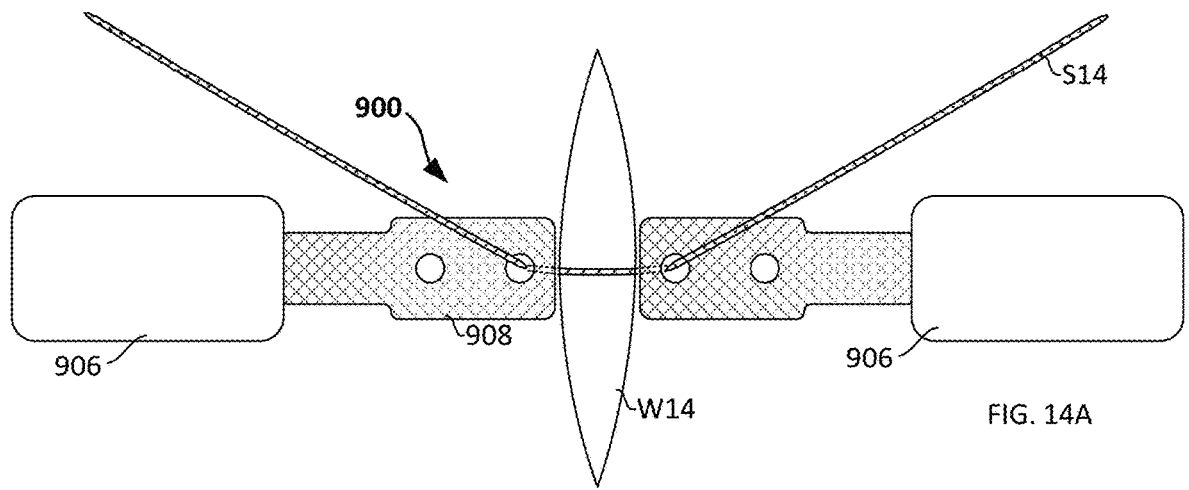
Figure 14B:
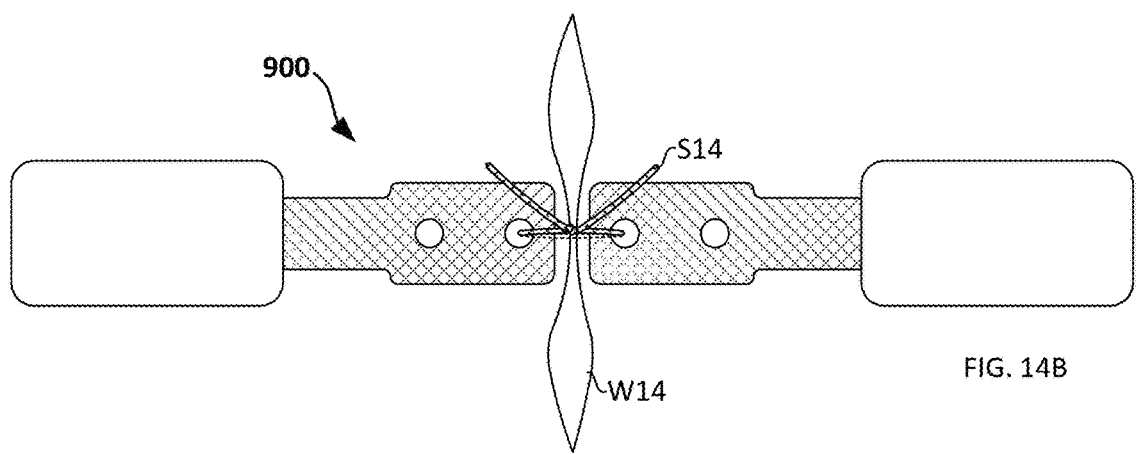
Figure 14C:
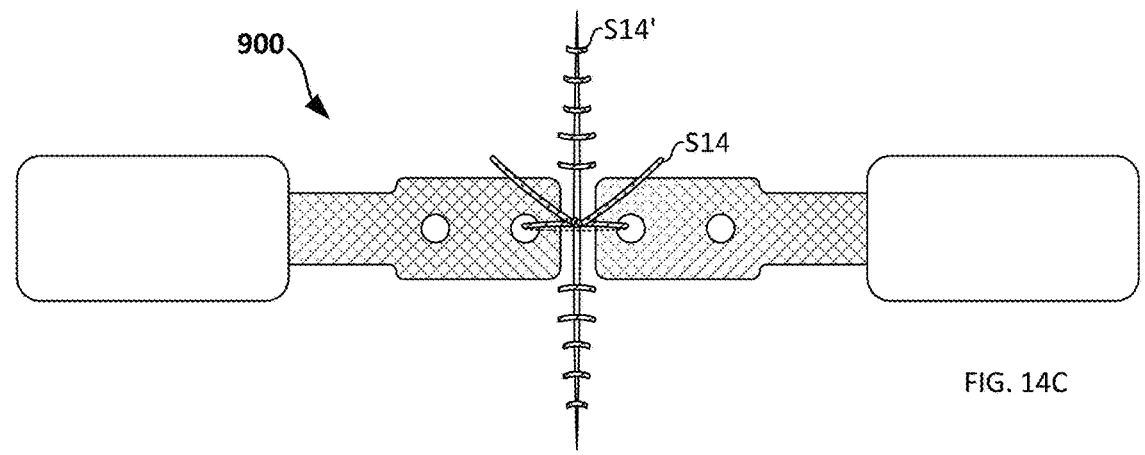
Figure 15A:
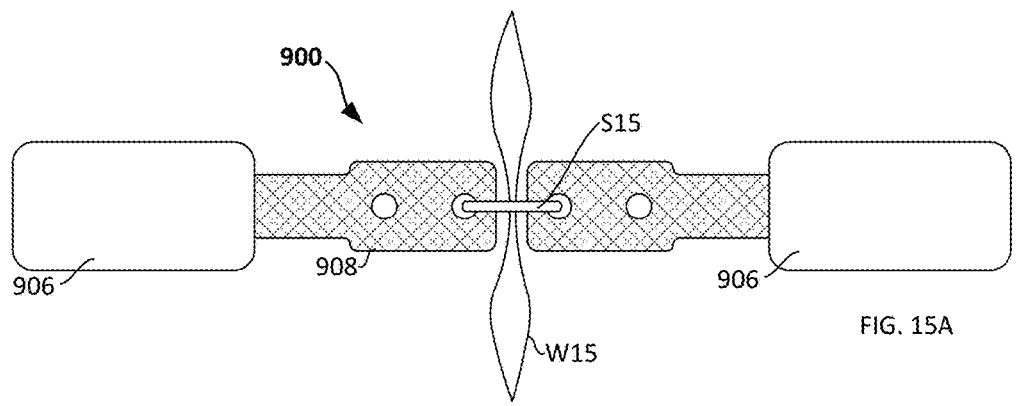
Figure 15B:
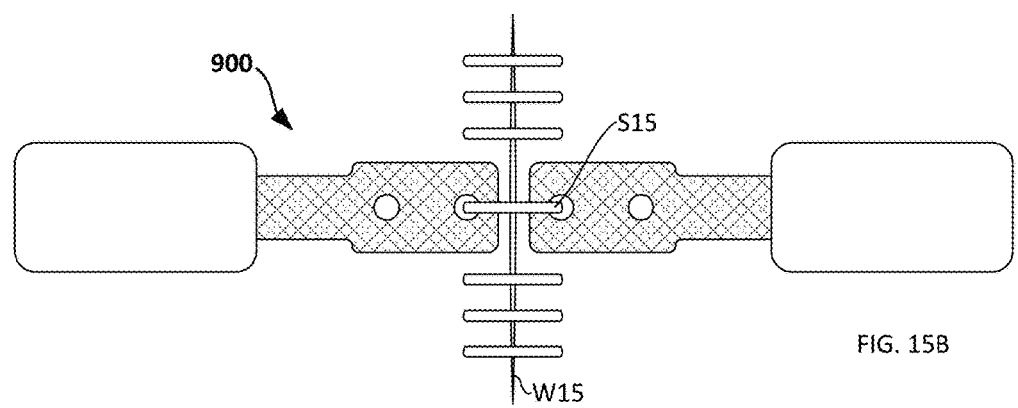
Figure 15C:
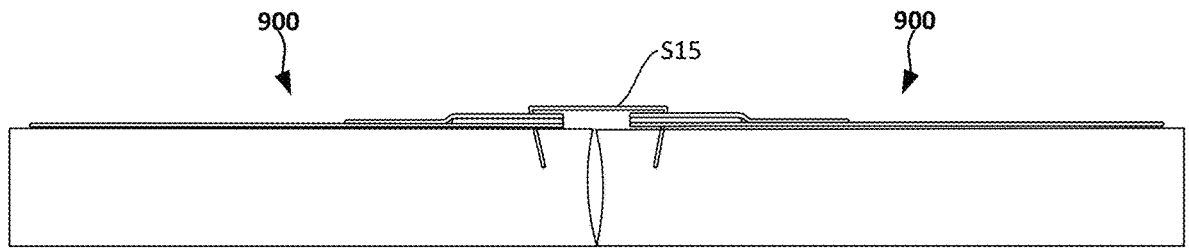
Figure 16A:
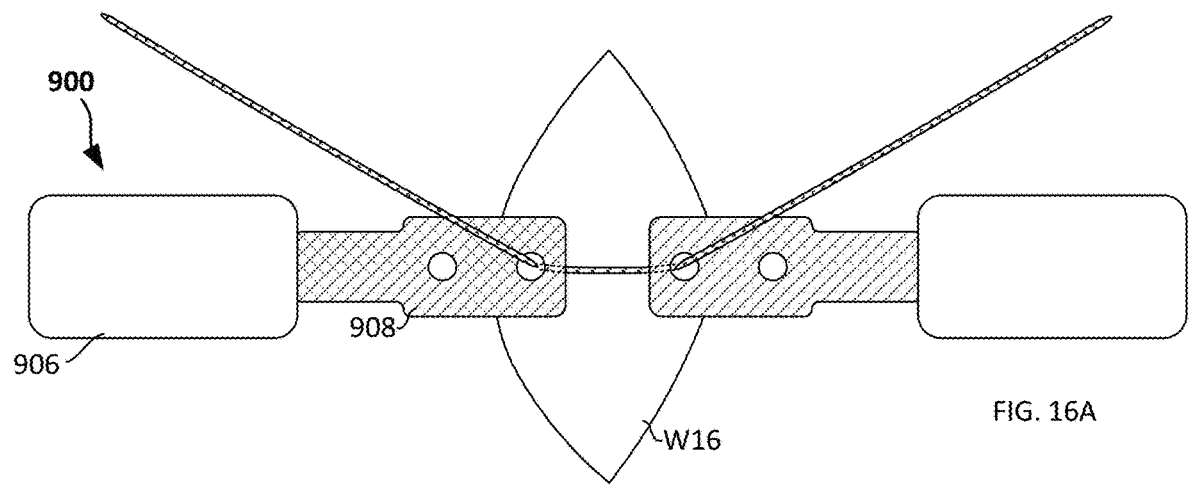
Figure 16B:
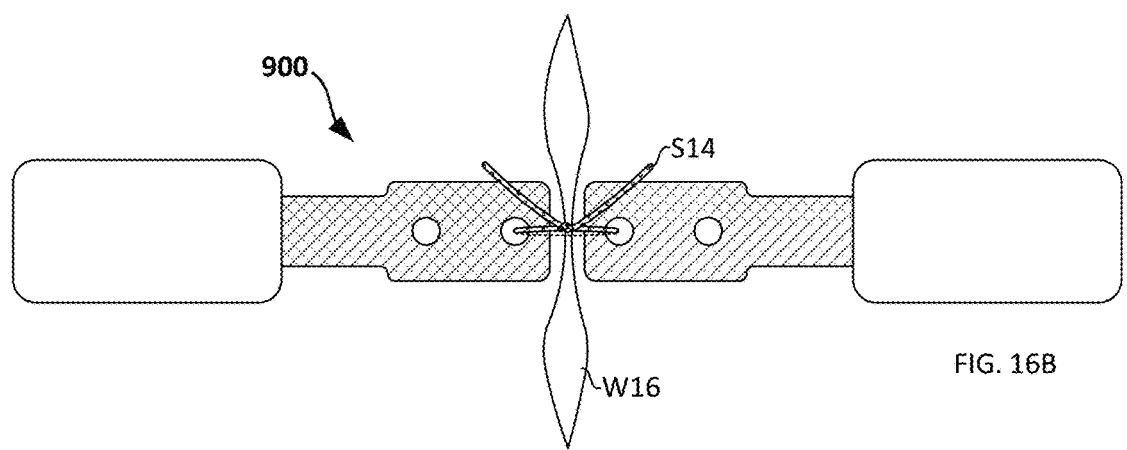

FIGS. 4A-F are schematic illustrations showing various suture patterns;

FIGS. 5A-C are alternative embodiments of a hemi-bridge having inserts of various shapes;

FIGS. 6-7 are schematic top and side views of variations of hemi-bridges having interdigitation features;

FIGS. 8 and 9 are schematic illustrations showing side and top views of a hemi-bridge according to yet another embodiment;

FIG. 10 is schematic top and side views of the insert of the hemi-bridge of FIGS. 8 and 9;

FIG. 11 includes perspective top and bottom views of the hemi-bridge of FIGS. 8 and 9, and a third perspective exploded view of the components of the hemi-bridge;

FIG. 12 is a schematic illustration showing a pair of hemi-bridges being used with one possible suture pattern to close a wound;

FIGS. 13A-B are schematic illustrations showing a side view of a flat hemi-bridge, and a top view of the flat hemi-bridge according to yet another embodiment;

FIGS. 13C-E are schematic top and side views showings several variations of the flat hemi-bridge of FIGS. 13A-B;

FIGS. 14A-C are schematic illustrations showing the use of the flat hemi-bridge device of FIGS. 13A-B;

FIGS. 15A-C are schematic illustrations showing the use of the flat hemi-bridge device with staples; and FIGS. 16A-B illustrate another example of using a flat hemi-bridge device of FIGS. 13A-B.

Various embodiments of the present invention will now be described with reference to the appended drawings. It is to be appreciated that these drawings depict only some embodiments of the invention and are therefore not to be considered limiting of its scope.

DETAILED DESCRIPTION

Despite the various improvements that have been made to wound closure devices, conventional methods suffer from some shortcomings as discussed above.

There therefore is a need for further improvements to the devices and methods used to help facilitate proper and quicker healing of a wound. Among other advantages, the present disclosure may address one or more of these needs.

Figure 1:
FIG. 1 is schematic cross-sectional view of a hemi-bridge according to one embodiment of the present disclosure.

FIG. 1 is schematic cross-sectional view of a hemi-bridge 100. Hemi-bridge 100 generally extends between a proximal end 102 and a distal end 104, the proximal end being relatively closer to the wound, and the distal end being relatively farther from the wound. Hemi-bridge may include an insert 105 sandwiched between two layers of material. As shown, the insert is sandwiched between two layers of material include a lower layer 106, and an upper layer 108. In some variations, one or more waterproof layers may be disposed above the upper or lower layers so that a total of two, three, or four layers may be formed, not including the insert.

Insert 105 may be formed of a rigid material. In some examples, the insert is formed of a thermoplastic material such as polypropylene, polyethylene terephthalate, polyethylene (LDPE and HDPE), polymethylmethacrylate, polyethylene terepthalate glycol (PTG) such as 10 MIL or 20 MIL PETG or as low as 1 MIL PETG, polydimethyl siloxane, polyoxymethylene, polycarbonate, polyamide and nylon, polyvinyl chloride, polyphenylene sulfide, acrylonitrilebutadienestyrene, polystyrene, polytetrafluoroethylene. Preferably the thermoplastic material may have a suitable melting temperatures. Insert 105 may be formed of other suitable materials such as metals.

Figure 2:
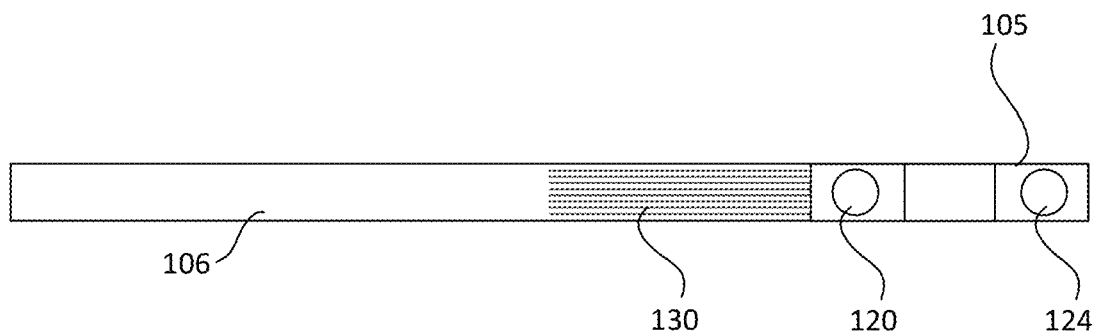
FIG. 2 is a schematic top view of the hemi-bridge of FIG. 1.

As shown, insert 105 may be stair-shaped, including a lower step 110, an inclined ramp 112 and an upper step 114, the inclined ramp connecting the two steps together. Insert 105 may have a length of approximately 5-20 mm, and preferably about 10 mm. Insert 105 may have a width that is approximately 2-6 mm, and a thickness of approximately 0.025 to 2 mm, depending on the material chosen. For example, a 20 MIL PETG insert may be 0.5 mm thick, a 10 MIL PETG insert may be 0.25 mm thick and a 1 MIL PETG insert may be 0.025 mm thick. In at least some examples, the upper step may be elevated by approximately 2 to 5 mm. In at least some examples, the lower and upper steps are of a same length, or approximately a same length. Insert 105 may have a generally constant single thickness along the lower step, the inclined ramp and the upper step. As best shown in FIG. 2, each of the upper and lower steps 110,114 may include a respective eyelet 120,124 for receiving a suture. In at least some examples, the eyelets are circular and of a same size as shown. Alternatively, eyelets may be formed of other shapes, such as oval, rectangular, triangular, etc. Eyelets 120,124 may allow the hemi-bridge to be used with various suturing configurations including simple, pulley and vertical mattress configurations, as will be described in more detail below. It will be understood that an insert may instead include only a single eyelet, or more than two eyelets (e.g., three, four, five or more eyelets).

Insert 105 may be disposed on one end of the device, in this case adjacent the proximal end 102, and may be substantially or entirely covered by lower and upper layers 106,108. Lower and upper layers 106,108 may be formed of rectangular strips of material, such as those typically used as a dressing. In some examples, the lower and upper layers or strips are approximately 50 mm in length, and 5-25 mm in width. In some examples, the lower and upper layers have the same width as the insert or are slightly wider than the insert. In some examples, the lower and/or upper layers are substantially longer than they are wide (e.g., 2×, 3×, 4×, 5× or 6× longer than they are wide). This length to width ratio may provide adequate surface area of adhesion over which to spread the tension. A longer upper and/or lower material may also reduce and/or eliminate the tilting effect of the insert's upper step falling over to contact the lower layer of material.

The upper and lower layers 106,108 may be formed of the same or similar material, size and/or configuration. Alternatively, the upper and lower layer may share some characteristics or may be formed of a different material, size and/or configuration.

Lower layer 106 may be formed of a woven, or non-woven material. In some examples, the lower layer includes a suitable non-woven material that prevents the absorption of blood and/or fluids. One example of a suitable material is STERI-STRIP® reinforced adhesive skin closures. In some examples, lower layer 106 may have an adhesive lower surface that will be in contact with the skin. Alternatively, both surfaces of the lower layer 106 may have an adhesive. The material of lower layer 106 may be isotropic (i.e., it has equal elasticity in any direction along its plane). Alternatively, the material of lower layer 106 may be anisotropic (i.e., it has variable elasticity in at least two directions along its plane).

In some examples, lower layer 106 may be reinforced with longitudinally-oriented polymer filaments or fiberglass strands (e.g., filaments 130 in FIG. 2) that results in anisotropic characteristics so that the material does not stretch along its longitudinal axis, but does stretch in lateral directions. FIG. 2 shows one example of a hemi-bridge having an insert 105 disposed on a lower layer 106, the lower layer having longitudinally-oriented filaments 130. For the sake of simplicity, the upper layer is not shown. As shown in FIG. 2, the filaments may be located along only a portion of the length of the lower layer. Thus, filaments 130 may extend along the entire length of the lower layer, more than half of the length of the lower layer, half of the lower layer, or less than half of the length of the lower layer (e.g., the filaments may extend along 100%, 90%, 80%, 70%, 60%, 50%, 40%, 30%, 20% or less of the length of the lower layer). Alternatively, lower layer 106 may include no filaments at all. That is, lower layer may be isotropic, or may be anisotropic without the use of filaments through the use of other techniques. The lower layer may be isotropic at one end, and anisotropic at another end (e.g., it may include filaments at the proximal end where the insert is disposed, and no filaments on the opposite end). In some example, the lower layer may be selected to prevent or reduce the possibility of skin maceration.

Upper layer 108 may be formed of a woven, or non-woven material. In some examples, the upper layer includes a suitable non-woven material that prevents the absorption of blood and/or fluids. In some examples, upper layer 108 may have an adhesive lower surface that will be in contact with the insert or the lower layer. The material of upper layer 108 may be isotropic (i.e., it has equal elasticity in any direction along its plane). Alternatively, the material of upper layer 108 may be anisotropic (i.e., it has no stretch in at least one direction along its plane).

In some example, upper layer 108 may also be reinforced with longitudinally-oriented polymer filaments or fiberglass strands that results in anisotropic characteristics so that the material does no stretch along its longitudinal axis, but does stretch in lateral directions. Filaments 130 may extend along the entire length of the upper layer, more than half of the length of the upper layer, half of the upper layer, or less than half of the length of the upper layer (e.g., 100%, 90%, 80%, 70%, 60%, 50%, 40%, 30%, 20% or less). Alternatively, upper layer 108 may include no filaments at all. That is, upper layer may be isotropic, or may be anisotropic without the use of filaments. The upper layer may be isotropic at one end, and anisotropic at another end (e.g., it may include filaments at the proximal end where the insert is disposed making it inelastic or less elastic in a longitudinal direction, and no filaments on the opposite end making it more elastic in the longitudinal direction).

By choosing the appropriate elasticity for the upper and/or lower layers (e.g., isotropic vs. anisotropic), an impedance mismatch between the skin and the lower layer of material may be lowered, reducing the possibility of blister formation. Blister formation may result from non-yielding materials adherent to the skin as tension imparted to the skin creates shearing forces in the horizontal plane of the skin that separate layers of the skin from one another (e.g., separating the epidermis from the dermis). In some examples, the presence of anisotropic segments that can mimic the elasticity of the underlying skin at predefined locations within the upper and/or lower layer may alleviate the shearing forces at certain positions. In some examples, the presence of isotropic segments at predefined locations within the upper and/or lower layer may alleviate the shearing forces at certain positions. Additionally, filaments in the upper and/or lower layers may serve to stabilize the insert to keep it upright, and prevent it from tipping.

As previously noted, upper and lower layers may share some or all of the characteristics. For examples, the two layers may be formed of the same material, may have the same non-woven construction, may include the same type of adhesive, may have the same elasticity profile, and/or the same extent, direction, amount and/or orientation of filaments.

Figure 3:
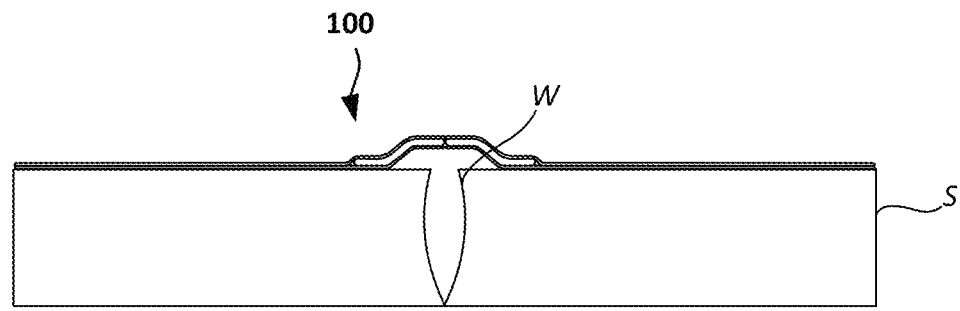
FIG. 3 is a schematic cross-sectional view showing a pair of hemi-bridges being used to close a wound.

In use, a hemi-bridge 100 may be laid flat on the skin surface on both sides of the wound, the lower layer of material contacting the skin surface. The edge of the hemi-bridge 100 may be disposed at the edge of the wound, or may be set back from the wound by 2 to 5 mm. Preferably, an adhesive on the lower surface of the lower layer couples the lower layer to the skin. The stair-shaped insert 105 is disposed above the lower layer and covered by the upper layer. In at least some examples, two hemi-bridges 100 are used, the two bridges facing one another and being disposed on either side of a wound "W" (FIG. 3). A suture pattern may be used to gather the ends of the wound with the hemi-bridges. Details of the various patterns will be described below. However, generally, the hemi-bridges may be brought together such that the upper steps of the two hemi-bridges come in contact with one another when gathered by the sutures. Alternatively, only a single pair of hemi-bridges may be used. Multiple pairs of hemi-bridges (e.g., 4 hemi-bridges) may also be used in some examples.

Figure 4A:
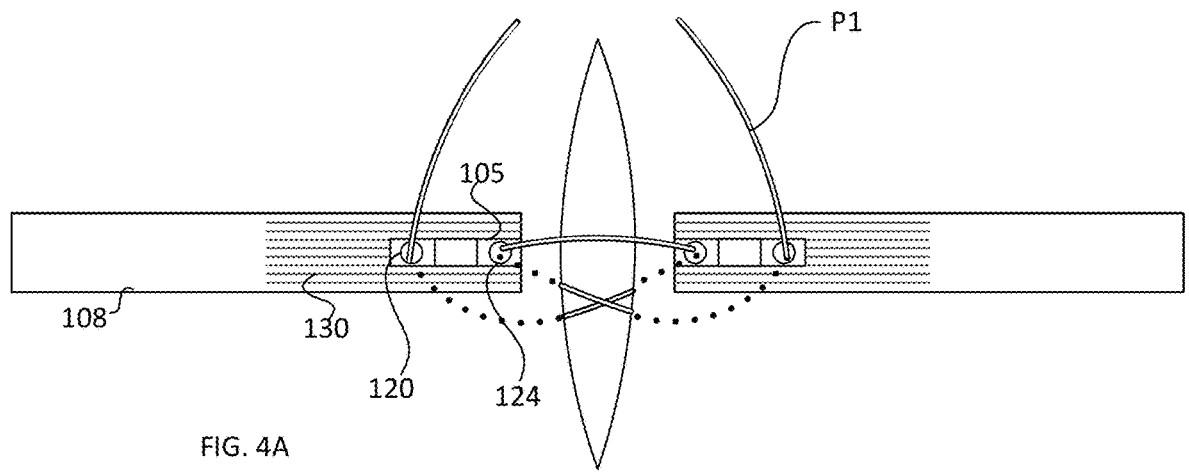
Figure 4B:
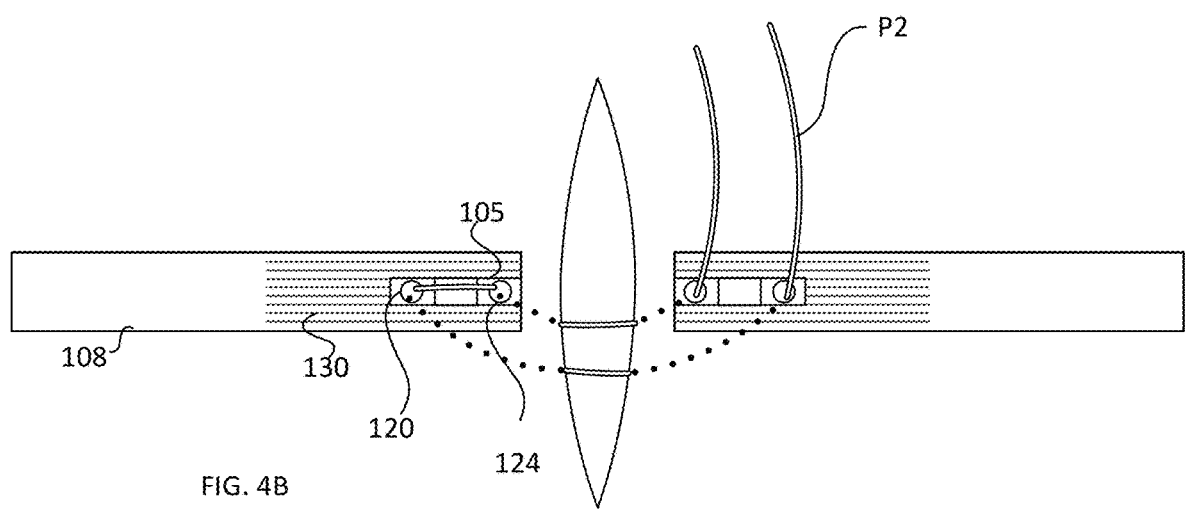
Figure 4C:
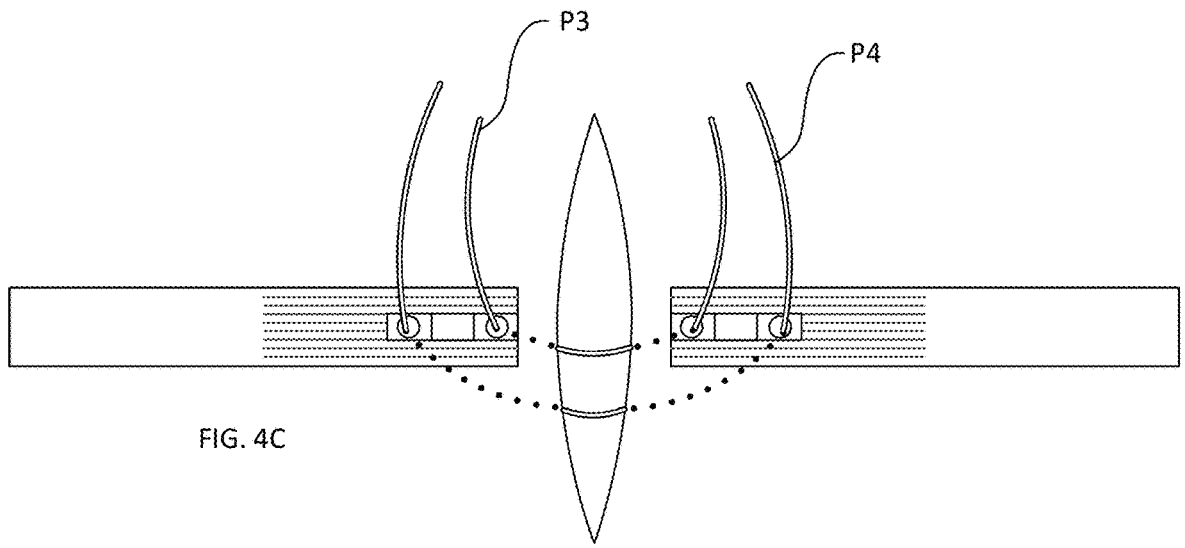
Figure 4D:
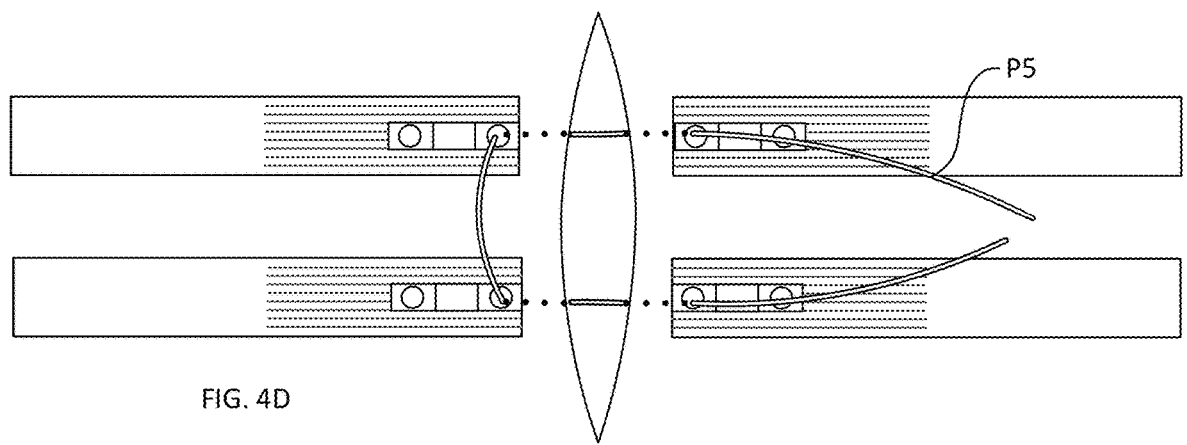
Figure 4E:
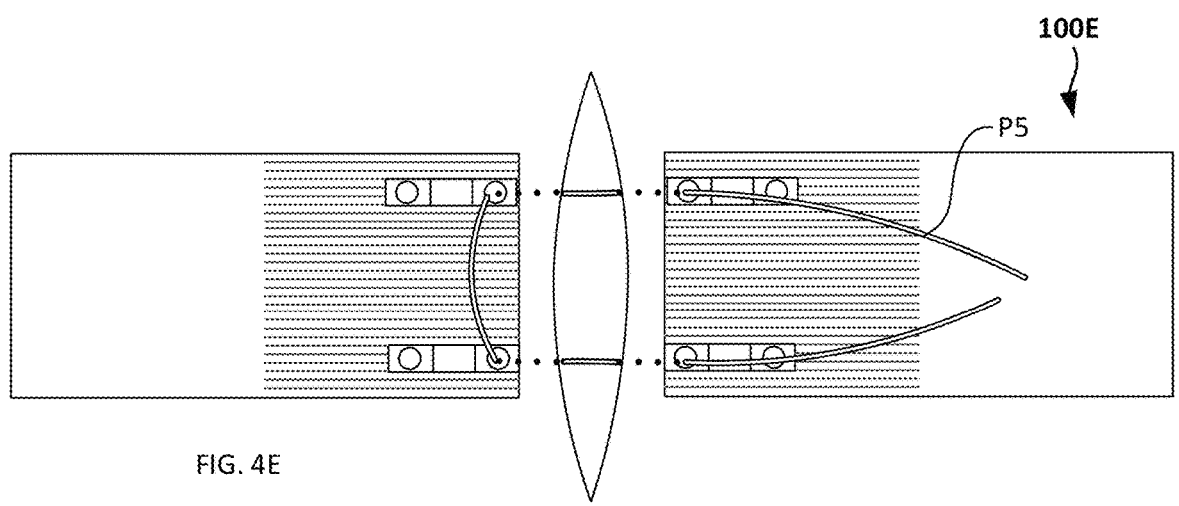

FIGS. 4A-C illustrate various suture patterns P1-P5 being used to gather ends of a wound using exemplary hemi-bridges. In FIG. 4A, a far-near-near-far pulley suture pattern P1 is formed with the suture. In this case, far refers to passing through an eyelet 120 on the lower step, while near refers to passing through an eyelet 124 on the upper step, and the "far-near-near-far" refers to the sequence in which the suture passes through these eyelets. In this and other examples, a dotted line indicates that the suture is under the skin and/or hemi-bridge and cannot be seen from a top view. In FIG. 4B, a far-far-near-near vertical mattress suture pattern P2 is shown. In FIG. 4C, two possible suture patterns P3,P4 are shown, the first being a simple interrupted near-near suture pattern P3, and the second being a simple interrupted far-far suture pattern P4. Finally, in FIGS. 4D-E, horizontal mattress suture patterns P5 are shown. In FIG. 4D, two hemi-bridges are disposed on either side of the wound, for a total of four hemi-bridges, each hemi-bridge being vertically aligned with another hemi-bridge adjacent to it, and horizontally aligned with an opposing hemi-bridge opposite the wound. Instead of using multiple hemi-bridges on either side of the wound, a compound hemi-bridge may be formed as shown in FIG. 4E, the compound hemi-bridge having widened upper and lower layers of material, and two or more inserts sandwiched between the layers (e.g., two, three, four, five or more inserts) and aligned with one another. Optional filaments are shown in this configuration, the filaments being located on one or two sides of the either the upper layer, the lower layer, or both.

Using any of the suture patterns described above, or other suitable one, a physician may apply tension to the suture of up to 10 or 20 Newtons to gather the two ends of the wound together. The hemi-bridges, and specifically the inserts, may act to elevate the suture above the wound, and may allow the physician to apply more force than possible without the use of the hemi-bridges. Moreover, the use of device having a rigid insert as described may prevent cheesewiring of a suture closing a wound under tension. For example, a wound closed under 20 Newtons of force without the present devices would likely suffer from cheesewiring of the suture through the skin. However, by using any of the present devices and techniques, the force of the suture may be substantially borne by the insert, and then transmitted to the entire area of the device, the relatively large surface area of the device being helpful in prevent injury or damage to the patient's skin. Additionally, elevation of the suture may reduce the likelihood of "track marks" on the patient's skin.

In some examples, the shape of the insert may be different. For example, FIG. 5A shows a hemi-bridge structure 500a having a proximal end 502 and a distal end 504, a wedge-shaped insert 505a having a step and upper and lower layers of materials 506,508 sandwiching the insert. FIG. 5B shows a hemi-bridge structure 500b having a proximal end 502 and a distal end 504, a ramp-shaped insert 505b and upper and lower layers of materials 506,508 sandwiching the insert. Any of the inserts in FIGS. 1-6 may be used to elevated the suture above the wound surface.

Figure 4F:
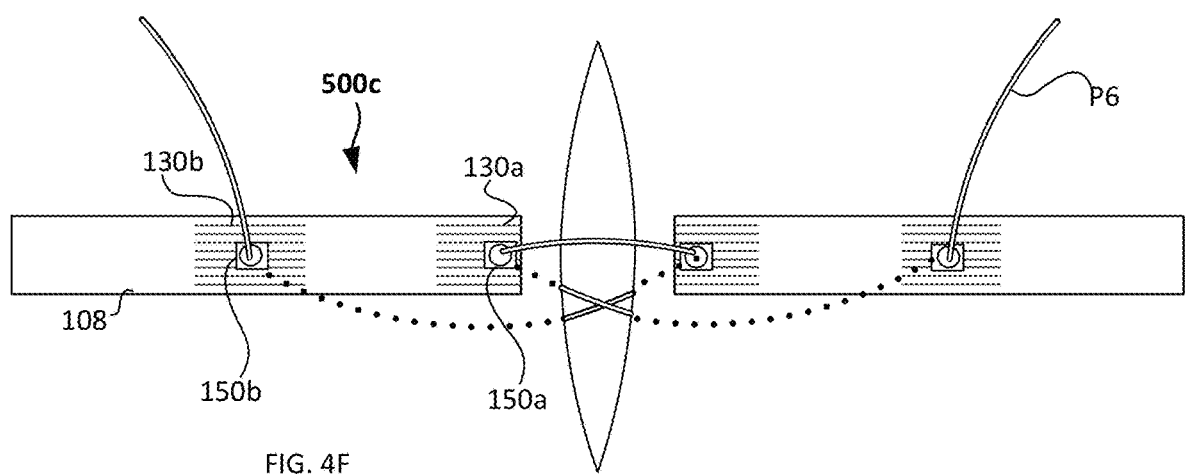

FIG. 5C shows another example in which two separate steps are formed instead of a continuous hemi-bridge. Specifically, bridge 500c includes a first step 150a and a second step 150b, the height of the first step being greater than the height of the second step. Alternatively, the first and second steps 150a,150b may be of a same height. Each step may include an eyelet as described above. The two steps are not directly connected to another, but are both sandwiched by upper and lower layers of material. In at least some examples, the upper and/or the lower layer of material includes sets of filaments 130a,130b disposed adjacent each of the steps, but the spacing between the two steps does not include such materials. One example of this embodiment in use is shown in FIG. 4F, in which bridge 500c is being used in a pulley suture arrangement P6.

Additionally, the top step of the insert may have interdigitation including a series of spaced projections 606 and depressions 607 so that two opposing hemi-bridges 605a, 605b may mate together with the projections and valleys of the two hemi-bridges interlocking with one another when the two components come together (FIG. 6). FIG. 7 illustrates another example of interdigitation where the hemi-bridges 705a,705b include a high-low tooth configuration arranged to mate with one another and form a complete bridge.

To manufacture the hemi-bridges, a rigid or substantially rigid insert such as those described above (e.g., a thermoplastic insert) may be sandwiched between upper and lower layers in a large sheet. The components may be die cut to the appropriate size, and holes may be formed in the insert to create eyelets. The assembly may be placed in a heated press, the press having a temperature that exceeds the melting temperature of the insert, but be below the safe temperature of the upper and lower layers. The heated press may also include an elevated portion to create the step in the insert. In addition to forming the step in the insert, the heated press may also reduce the presence of sharp edges at the bottom of the hemi-bridge by curling the sides of the device upward to redirect lower edges away from the skin of the patient. After proper heating, the assembly may be removed and cooled. The finished device may then be used to close a wound as described above. Alternatively, the insert may be formed separately (via injection molding, 3D printing or other techniques) and later coupled to the upper and lower layers.

The suture securing devices, systems, and methods described herein may be used to secure a suture and reduce or eliminate the likelihood that a suture may become inflamed, infected, ingrown, and/or reopened and increase the length of time that the suture can remain in place, among other purposes. Additionally, the devices disclosed herein may be capable of allowing a physician to apply a large force when tying a suture without damaging nearby tissue, and in some cases may be used to avoid the usage of skin grafts to close relatively large wounds.

FIG. 8 is schematic cross-sectional view of a hemi-bridge 800 according to yet another embodiment. Hemi-bridge 800 generally extends between a proximal end 802 and a distal end 804, the proximal end being relatively closer to the wound, and the distal end being relatively farther from the wound. Hemi-bridge may include an insert 805 sandwiched between two layers of material. Specifically, the two layers of material include a lower layer 806, and an upper layer 808. Lower and upper layers 806,808 may be coupled together via an adhesive where they are in contact. Additionally, insert 805 may be coupled via adhesive, or other suitable means, to the top of the lower layer 806 and/or the bottom of the upper layer 808.

Insert 805 may be formed of any of the materials discussed above with reference to insert 105, such as various thermoplastics and/or metals, and lower and upper layers 806,808 may be formed of the same materials as lower and upper layers 106,808. As shown, insert 805 may be stair-shaped and includes a lower step, an inclined ramp and an upper step similar to the configuration of FIG. 1. As best shown in FIG. 9, each of the upper and lower steps may include a respective eyelet 820,824 for receiving a suture. In at least some examples, the eyelets are circular and of a same size as shown, or may be in any of the configurations previously described.

Hemi-bridge 800 may be divided into three zones, z1,z2, z3. First zone z1 may include insert 805 sandwiched between lower and upper layers 806,808. Second zone z2 may include only the lower and upper layers 806,808 without the insert 805. Third zone z3 may include only a single material, such as lower layer 806. The three zones z1-z3 may form differential stiffness zones that become less stiff further from the wound edge (e.g., greatest stiffness at proximal end 802 and smallest stiffness at distal end 804). First zone z1 provides the greatest stiffness, primarily due to the presence of the essentially inelastic insert 805. Second zone z2 may be less stiff with its bi-layer of non-woven material (e.g., lower layer 806 and upper layer 808), which may be fused with an adhesive or coupled together in any suitable manner. Third zone z3 may be the least stiff with a monolayer of non-woven material (e.g., only lower layer 806 or only upper layer 808) and may serve as the most reliable adhesive zone.

Without being bound by any particular theory, it is believed that in the vicinity of the wound (i.e., closer to first zone z1) will be exposed to more fluid. All dressings have a tendency to lose adhesion with a certain distance of the edge of the dressing. For example, a 10 mm dressing may have 1-2 mm of loss of edge adhesion due to moisture, etc. Thus, after a few days, a 10 mm wide strip may really only have 6-8 mm of useful adhesion with further deterioration thereafter. Thus, having a wider and longer third zone, z3, may provide much more width prior to losing adhesion and will also tend to reduce shear through higher cross-sectional surface area.

In some examples, insert 805 may be formed as a flat piece that is bent to include a step as previously discussed. In at least some examples, the step forms an angle θ of between 20 and 60 degrees. In at least some examples, the angle θ is between 30 and 50 degrees. In at least some examples, the angle θ is equal to or approximately 40 degrees as shown in FIG. 10.

As shown in the perspective views, the lower and upper layers 806,808 and the insert 805 may have a shape and a size that matches other components adjacent thereto. For example, both the lower and upper layers 806,808 may have a generally rectangular stepped-shape that matches the insert 805 at first zone z1. Both lower and upper layers 806,808 may have a narrowed neck at second zone z2, and lower layer 806 may have a wider and longer rectangular shape at third zone z3.

In at least some examples, the hemi-bridge has a total length of approximately 2 to 3 mm, or about 2.3 to 2.4 mm. Third zone z3 may have a length that is 40% to 50% of the total length of the hemi-bridge. First and second zones z1,z2 may be approximately equal in length, or first zone z1 may be slightly longer than second zone z2. Third zone z3 may be the widest of the three zones, and may have a width of between 0.5 and 0.6 mm. Second zone z2 may be the narrowest and may have a width of between 0.3 and 0.35 mm. First zone z1 may have wider than second zone z2 and narrower than third zone z3 and may have a width of between 0.4 and 0.5 mm. The surface area may be greatest in third zone z3 and smallest in second zone z2. Insert 805 may have a thickness of between 0.010 mm and 0.030 mm and specifically about 0.020 mm.

In at least some examples, two hemi-bridges 800 are used, the two bridges facing one another and being disposed on either side of a wound "W" (FIG. 12). A suture pattern may be used to gather the ends of the wound with the hemi-bridges using any of the suturing techniques and patterns described above with reference to the other embodiments. However, generally, the hemi-bridges may be brought together such that the upper steps of the two hemi-bridges approach each other, or come in contact with one another when gathered by the sutures.

Although the hemi-bridges have been disclosed as having an insert including an upper step, a lower step and a connecting ramp, other variations are possible. For example, instead of having an inclination angle as previously described, the insert may be completely flat. For example, hemi-bridge 900 extends between ends 902,904 and include a planar insert 905 that is covered by lower layer 906 and upper layer 908 (FIGS. 13A-B). It will be understood that in manufacturing the device, upper and lower layers of material may sandwich an insert and form a configuration similar to the flat configuration of FIGS. 13A-B. The flat sandwich of lower layer-insert-upper layer may be collectively die cut before thermoforming at a high temperature (e.g., 200 degrees F.) to form an inclined angle and any number of steps. It will be understood that the flat configuration may be used in certain applications, and that other applications may require thermoforming to provide an angle of 10, 20, 30, 40, 50 or 60 degrees. Thus, the angle of inclination may be formed as desired for a specific application.

Even without an inclination, the flat configuration of hemi-bridge 900 may elevate a suture or other fastening element via insert 905 to achieve one or more of the advantages described above. In at least some examples, the lower layer 906 is formed of a non-woven polyester with an adhesive backing, insert 905 is formed of PETG, and upper layer 908 is formed of polyethylene. In at least some examples, the lower layer 906 may also partially or entirely include an elastic tape having variable thickness such as Microfoam tape made by 3M®, the tape being capable of having variable elasticity due to the variable thickness. The non-woven polyester lower layer 906 may have the PETG insert adhered to its top surface at one end, the inert having one or more (e.g., two) eyelets. Due to the layering of material, a stepped configuration having three zones, z1,z2, z3 is formed, first zone z1 having all three layers, second zone z2 having two layers, and third zone z3 having only the lower layer.

As shown in FIG. 13B, third zone z3 may be the widest portion of the device 900 with only a single layer of stretchable and absorbent adhesive material. The material of lower layer may experience a high amount of strain under force, so an elastic material may be used to allow less shear force on the trailing edge, a common problem in adhesive dressings. Second zone z2 may be a narrowed central portion of two layers. In addition to the lower layer, the second zone may have a polyethylene upper layer 908 to resist blood and fluid from being absorbed into the dressing. The polyethylene layer may also provide strength and reinforcement for the narrow central zone. First zone z1 may be the strongest and most rigid due to the presence of the insert 905. Insert 905 may resist tearing under high tension (e.g., up to 20N or 30N of force) and may also elevate the suture material above the skin.

First and second zones z1,z2 may allow blood to be wiped off the device and provide a stiff connection to third zone z3, where shear forces are reduced by the single layer of lower stiffness material. Thus, different regions may be formed with increasing elasticity from first zone z1 closer to the wound toward third zone z3 farthest from the wound. That is, first zone z1 may have the lowest elasticity, second zone z2 may have an intermediate elasticity, and third zone z3 may have the greatest elasticity. Conversely, first zone z1 may have the greatest stiffness, second zone z2 may have an intermediate stiffness that is less than the stiffness of first zone z1, and third zone z3 may have the lowest stiffness compared to the other three zones. The device 900 also increases in height as it gets closer to the wound to provide elevation.

Without being bound by any particular theory, it is the believed that the suture acts to not only apply tension to gather the wound, but also applies a downward force on the rigid insert. This downward force is helpful to keep a consistent contact of the adhesive of the lower layer with the skin. Additionally, a planar rigid insert may evenly distribute this pressure on the skin, and the downward force may reduce the likelihood of maceration.

FIGS. 13C-E are schematic top and side views showings several variations of the flat hemi-bridge of FIGS. 13A-B. In FIG. 13C, a hemi-bridge device 900C is formed that is similar to that of FIGS. 13A-B, but excludes the tailored or narrowed neck in second zone z2. Instead, the lower and upper layers present a continuous width that is present in first and second zones z1,z2 as shown, while third zone z3 is wider than both.

In FIG. 13D, a hemi-bridge 900D includes the narrowed neck formed in second zone z2, but the upper layer 908C partially extends over the wider portion of lower layer 906 as shown so that second zone z2 having two layers of material is slightly longer than the embodiment of FIGS. 13A-B. In this example, upper layer 908C may have three widths including a first width adjacent the insert, a second width at the tailored neck and a third width at the wider region of the lower layer. It will be understood that the embodiments of FIGS. 13C and 13D may be combined so that the upper layer only includes a constant first width adjacent the insert and a majority of the second zone z2, and a second width overlying the wider region of the lower layer.

FIG. 13E illustrates yet another embodiment of a hemi-bridge 900E, the hemi-bridge having a lower layer 906, an insert 905 and an upper layer 908 as described above. Hemi-bridge 900E further includes a covering layer 912, formed of a waterproof material, the covering layer 912 being disposed on and partially or fully extending over the upper layer 908. Covering layer 912 may be of the same length as upper layer 908 and may be disposed in first zone z1, and extend into second zone z2 to provide additional stiffness to second zone z2.

In use, two hemi-bridge devices 900 may be laid flat on the skin surface on either side of the wound, the lower layer of the device contacting and being adhered the skin surface (FIG. 14A). The edge of the hemi-bridge 900 may be disposed at the edge of the wound W14, or may be set back from the wound W14 by 2 to 5 mm. A suture S14 may enter a first eyelet of the first hemi-bridge, pierce the skin and traverse the wound through the underlying tissue, exiting the first eyelet of the second hemi-bridge as shown in FIG. 14A. Suture S14 may be used to gather the margins of the wound and a knot may be tied (FIG. 14B). Generally, the hemi-bridge devices are disposed near the middle of the wound as shown, although different configurations are possible. With the center of the wound gathered (FIG. 14B), additional sutures S14' may be used to gather edges of the wound and completely close the wound (FIG. 14C).

It will be understood that other ways of using the hemi-bridge devices are possible. For example, as shown in FIGS. 15A-C, surgical staples S15 or clips may be used instead of sutures to close wound W15 and may extend through any of the eyelets of the insert. Additionally, combinations of various kinds of fastening elements (e.g., sutures, clips, staples, etc.) may be used, and the eyelets of the device may be configured to accept any or all kinds of fastening elements.

In another example (FIG. 16A-B), hemi-bridge devices may be used to close larger wounds W16. In this example, wound W16 may have missing underlying tissue such that piercing and traversing the underlying tissue is difficult or impossible. In such a case, a suspended suture S16 may be used to gather tissue without traversing the underlying tissue. In one example, skin may be missing below zone z1 of the device, but may be present in zones z2 and z3. In such a situation, a suture may not pierce the skin adjacent first zone z1, but the hemi-bridge device may remain secured to the skin via zones z2 and z3 only.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A suture elevating device, comprising:
an insert having at least one eyelet; and
at least one member of an upper layer of material at least partially disposed over the insert, and a lower layer of material disposed below the insert, the lower layer of material having an adhesive disposed on a lower surface;
wherein the insert, the upper layer and the lower layer form three zones, each of the zones having a different elasticity and stiffness than others of the zones, the three zones including a first zone having the insert sandwiched between the upper layer and the lower layer, a second zone having only the upper layer and the lower layer coupled together, and a third zone having only the lower layer, and wherein the first zone has a first elasticity, the second zone has a second elasticity, and the third zone has a third elasticity, and the third elasticity is greater than both the second elasticity and the first elasticity.

2. The suture elevating device of claim 1, wherein the at least one member includes both the upper layer and the lower layer.

3. The suture elevating device of claim 2, wherein the upper layer partially covers the lower layer and fully covers the insert.

4. The suture elevating device of claim 2, wherein the lower layer is longer than the upper layer.

5. The suture elevating device of claim 1, wherein the multiple zones have varying thicknesses.

6. A suture elevating device comprising:
an insert having at least one eyelet;
at least one member of an upper layer of material at least partially disposed over the insert, and a lower layer of material disposed below the insert, the lower layer of material having an adhesive disposed on a lower surface; and
a waterproofing layer comprising polyethylene, the waterproofing layer extending over both the insert and the upper layer;
wherein the insert, the upper layer and the lower layer form multiple zones, each of the zones having a different elasticity and stiffness than others of the zones.

7. The suture elevating device of claim 1, wherein the third zone has a greatest length and a greatest width of the three zones.

8. The suture elevating device of claim 1, wherein the third zone has a greatest surface area of the three zones.

9. The suture elevating device of claim 1, wherein the second zone is the narrowest of the three zones.

10. The suture elevating device of claim 1, wherein the second zone includes an adhesive coupling the upper layer to the lower layer.

11. A system, comprising:
a suture-elevating device including a pair of hemi-bridges, each of the pair of hemi-bridges having i) an insert with at least one eyelet, and ii) at least one member of an upper layer of material at least partially disposed over the insert, and a lower layer of material disposed below the insert, the lower layer of material having an adhesive disposed on a lower surface, wherein the insert, the upper layer and the lower layer form three zones, each of the zones having a different elasticity and stiffness than others of the zones, the three zones including a first zone having the insert sandwiched between the upper layer and the lower layer, a second zone having only the upper layer and the lower layer coupled together, and a third zone having only the lower layer, and wherein the first zone has a first elasticity, the second zone has a second elasticity, and the third zone has a third elasticity, and the third elasticity is greater than both the second elasticity and the first elasticity; and
a fastening element coupling the pair of hemi-bridges.

12. The suture elevating device of claim 11, wherein the at least one member includes both the upper layer and the lower layer.

13. The suture elevating device of claim 11, wherein the pair of hemi-bridges are similar in shape and size, and are configured to be disposed on opposite sides of a wound and aligned to face one another such that a first insert of a first hemi-bridge faces a second insert of a second hemi-bridge.

14. The suture elevating device of claim 11, wherein each of the pair of hemi-bridges includes a plurality of zones of varying thicknesses.

15. The suture elevating device of claim 11, wherein the fastening element is a suture.

* * * * *